United States Patent
Gillis et al.

(10) Patent No.: US 9,381,109 B2
(45) Date of Patent: Jul. 5, 2016

(54) SYSTEMS AND METHODS FOR TREATMENT OF SLEEP APNEA

(71) Applicant: ReVENT Medical, Inc., Newark, CA (US)

(72) Inventors: Edward M. Gillis, Livermore, CA (US); John H. Shadduck, Menlo Park, CA (US)

(73) Assignee: ReVENT Medical, Inc., Newark, CA (US)

( * ) Notice: Subject to any disclaimer, the term of this patent is extended or adjusted under 35 U.S.C. 154(b) by 0 days.

(21) Appl. No.: 14/289,475

(22) Filed: May 28, 2014

(65) Prior Publication Data

US 2014/0261451 A1 Sep. 18, 2014

Related U.S. Application Data

(62) Division of application No. 13/053,025, filed on Mar. 21, 2011, now Pat. No. 8,776,799.

(60) Provisional application No. 61/315,835, filed on Mar. 19, 2010, provisional application No. 61/315,838, filed on Mar. 19, 2010, provisional application No. 61/347,348, filed on May 21, 2010, provisional application No. 61/347,356, filed on May 21, 2010, provisional application No. 61/367,707, filed on Jul. 26, 2010, provisional application No. 61/418,238, filed on Nov. 30, 2010, provisional application No. 61/419,690, filed on Dec. 3, 2010.

(51) Int. Cl.
*A61F 5/56* (2006.01)
*A61F 2/00* (2006.01)

(52) U.S. Cl.
CPC ... *A61F 5/56* (2013.01); *A61F 2/00* (2013.01); *A61F 5/566* (2013.01); *A61F 2210/0004* (2013.01)

(58) Field of Classification Search
CPC combination set(s) only.
See application file for complete search history.

(56) References Cited

U.S. PATENT DOCUMENTS

| | | | |
|---|---|---|---|
| 4,424,208 A | 1/1984 | Wallace et al. |
| 4,582,640 A | 4/1986 | Smestad et al. |
| 4,978,323 A | 12/1990 | Freedman |
| 5,041,138 A | 8/1991 | Vacanti et al. |
| 5,145,935 A | 9/1992 | Hayashi |

(Continued)

FOREIGN PATENT DOCUMENTS

| | | |
|---|---|---|
| EP | 1216013 B1 | 6/2006 |
| EP | 2561842 A1 | 2/2013 |

(Continued)

OTHER PUBLICATIONS

Gillis et al.; U.S. Appl. No. 14/275,426 entitled "System and methods for treatment of sleep apnea," filed May 12, 2014.

(Continued)

*Primary Examiner* — Ophelia A Hawthorne
(74) *Attorney, Agent, or Firm* — Shay Glenn LLP

(57) ABSTRACT

A system for revisably treating an airway disorder is provided with an implant body configured to conform to an airway-interface tissue site in a manner compatible with normal physiological function of the site. In some embodiments, first and second openings extend through first and second implant ends, respectively, for permitting a tissue plug to grow through each opening. Methods of using and revising such systems are also provided.

22 Claims, 13 Drawing Sheets

(56) References Cited

U.S. PATENT DOCUMENTS

| | | | |
|---|---|---|---|
| 5,326,355 A | 7/1994 | Landi | |
| 5,372,600 A | 12/1994 | Beyar et al. | |
| 5,428,024 A | 6/1995 | Chu et al. | |
| 5,506,300 A | 4/1996 | Ward et al. | |
| 5,531,761 A | 7/1996 | Yoon | |
| 5,665,822 A | 9/1997 | Bitler et al. | |
| 5,697,779 A | 12/1997 | Sachdeva et al. | |
| 5,762,599 A | 6/1998 | Sohn | |
| 5,775,322 A | 7/1998 | Silverstein et al. | |
| 5,782,636 A | 7/1998 | Armstrong et al. | |
| 5,972,000 A | 10/1999 | Beyar et al. | |
| 5,972,111 A | 10/1999 | Anderson | |
| 5,979,456 A | 11/1999 | Magovern | |
| 5,988,171 A | 11/1999 | Sohn et al. | |
| 6,019,779 A | 2/2000 | Thorud et al. | |
| 6,161,541 A | 12/2000 | Woodson | |
| 6,165,486 A | 12/2000 | Marra et al. | |
| 6,197,043 B1 * | 3/2001 | Davidson | A61L 17/04 424/443 |
| 6,231,605 B1 | 5/2001 | Ku | |
| 6,250,307 B1 | 6/2001 | Conrad et al. | |
| 6,388,043 B1 | 5/2002 | Langer et al. | |
| 6,390,096 B1 | 5/2002 | Conrad et al. | |
| 6,395,017 B1 | 5/2002 | Dwyer et al. | |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,439,238 B1 | 8/2002 | Brenzel et al. | |
| 6,450,169 B1 | 9/2002 | Conrad et al. | |
| 6,453,905 B1 | 9/2002 | Conrad et al. | |
| 6,458,127 B1 | 10/2002 | Truckai et al. | |
| 6,467,485 B1 | 10/2002 | Schmidt | |
| 6,502,574 B2 | 1/2003 | Walter et al. | |
| 6,507,675 B1 | 1/2003 | Lee et al. | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,541 B2 | 2/2003 | Knudson et al. | |
| 6,523,542 B2 | 2/2003 | Knudson et al. | |
| 6,530,896 B1 | 3/2003 | Elliott | |
| 6,546,936 B2 | 4/2003 | Knudson et al. | |
| 6,569,191 B1 | 5/2003 | Hogan | |
| 6,578,763 B1 | 6/2003 | Brown | |
| 6,601,584 B2 | 8/2003 | Knudson et al. | |
| 6,626,181 B2 | 9/2003 | Knudson et al. | |
| 6,626,916 B1 | 9/2003 | Yeung et al. | |
| 6,629,988 B2 | 10/2003 | Weadock | |
| 6,634,362 B2 | 10/2003 | Conrad et al. | |
| 6,636,767 B1 | 10/2003 | Knudson et al. | |
| 6,703,040 B2 | 3/2004 | Katsarava et al. | |
| 6,748,950 B2 | 6/2004 | Clark et al. | |
| 6,748,951 B1 | 6/2004 | Schmidt | |
| 6,772,944 B2 | 8/2004 | Brown | |
| 6,899,105 B2 | 5/2005 | Krueger et al. | |
| 7,017,582 B2 | 3/2006 | Metzger et al. | |
| 7,063,089 B2 | 6/2006 | Knudson et al. | |
| 7,090,672 B2 | 8/2006 | Underwood et al. | |
| 7,107,992 B2 | 9/2006 | Brooks et al. | |
| D536,792 S | 2/2007 | Krueger et al. | |
| 7,192,443 B2 | 3/2007 | Solem et al. | |
| 7,213,599 B2 | 5/2007 | Conrad et al. | |
| 7,255,110 B2 | 8/2007 | Knudson et al. | |
| 7,322,356 B2 | 1/2008 | Critzer et al. | |
| 7,337,781 B2 | 3/2008 | Vassallo | |
| 7,793,661 B2 | 9/2010 | Macken | |
| 7,824,704 B2 | 11/2010 | Anderson et al. | |
| 7,909,037 B2 | 3/2011 | Hegde et al. | |
| 7,909,038 B2 | 3/2011 | Hegde et al. | |
| 7,934,506 B2 | 5/2011 | Woodson et al. | |
| 7,947,076 B2 | 5/2011 | Vassallo et al. | |
| 7,992,567 B2 | 8/2011 | Hirotsuka et al. | |
| 7,997,266 B2 | 8/2011 | Frazier et al. | |
| 8,167,787 B2 | 5/2012 | Gillis | |
| 8,186,355 B2 | 5/2012 | van der Burg et al. | |
| 8,220,466 B2 | 7/2012 | Frazier et al. | |
| 8,327,854 B2 | 12/2012 | Gillis et al. | |
| 8,409,296 B2 | 4/2013 | Knize et al. | |
| 8,523,760 B2 | 9/2013 | Gillis | |
| 8,528,564 B2 | 9/2013 | Paraschac et al. | |
| 8,707,960 B2 | 4/2014 | Gillis et al. | |
| 8,733,363 B2 | 5/2014 | Gillis et al. | |
| 8,747,296 B2 | 6/2014 | Gillis | |
| 8,776,799 B2 | 7/2014 | Gillis et al. | |
| 9,050,176 B2 | 6/2015 | Datta et al. | |
| 2001/0051815 A1 | 12/2001 | Esplin | |
| 2002/0020417 A1 | 2/2002 | Nikolchev et al. | |
| 2002/0116050 A1 | 8/2002 | Kocur | |
| 2002/0116070 A1 | 8/2002 | Amara et al. | |
| 2003/0149445 A1 | 8/2003 | Knudson et al. | |
| 2004/0045556 A1 | 3/2004 | Nelson et al. | |
| 2004/0139975 A1 | 7/2004 | Nelson et al. | |
| 2004/0204734 A1 | 10/2004 | Wagner et al. | |
| 2005/0004417 A1 | 1/2005 | Nelson et al. | |
| 2005/0065615 A1 | 3/2005 | Krueger et al. | |
| 2005/0090861 A1 | 4/2005 | Porter | |
| 2005/0092332 A1 | 5/2005 | Conrad et al. | |
| 2005/0115572 A1 | 6/2005 | Brooks et al. | |
| 2005/0121039 A1 | 6/2005 | Brooks et al. | |
| 2005/0154412 A1 | 7/2005 | Krueger et al. | |
| 2005/0171572 A1 | 8/2005 | Martinez | |
| 2005/0199248 A1 | 9/2005 | Pflueger et al. | |
| 2005/0267321 A1 | 12/2005 | Shadduck | |
| 2005/0274384 A1 | 12/2005 | Tran et al. | |
| 2006/0150986 A1 | 7/2006 | Roue et al. | |
| 2006/0201519 A1 | 9/2006 | Frazier et al. | |
| 2006/0207606 A1 | 9/2006 | Roue et al. | |
| 2006/0229669 A1 | 10/2006 | Mirizzi et al. | |
| 2006/0235380 A1 | 10/2006 | Vassallo | |
| 2006/0260623 A1 | 11/2006 | Brooks et al. | |
| 2006/0289014 A1 | 12/2006 | Purdy et al. | |
| 2006/0289015 A1 | 12/2006 | Boucher et al. | |
| 2007/0010787 A1 | 1/2007 | Hackett et al. | |
| 2007/0108077 A1 | 5/2007 | Lung et al. | |
| 2007/0144534 A1 | 6/2007 | Mery et al. | |
| 2007/0198040 A1 | 8/2007 | Buevich et al. | |
| 2007/0261701 A1 | 11/2007 | Sanders | |
| 2007/0288057 A1 | 12/2007 | Kuhnel | |
| 2007/0295340 A1 | 12/2007 | Buscemi | |
| 2008/0023012 A1 | 1/2008 | Dineen et al. | |
| 2008/0027560 A1 | 1/2008 | Jackson et al. | |
| 2008/0053461 A1 | 3/2008 | Hirotsuka et al. | |
| 2008/0058584 A1 | 3/2008 | Hirotsuka et al. | |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 * | 4/2008 | Buscemi | A61F 5/566 128/848 |
| 2008/0078412 A1 | 4/2008 | Buscemi et al. | |
| 2008/0082113 A1 | 4/2008 | Bishop et al. | |
| 2008/0188947 A1 | 8/2008 | Sanders | |
| 2009/0038623 A1 | 2/2009 | Farbarik et al. | |
| 2009/0044814 A1 | 2/2009 | Iancea et al. | |
| 2009/0084388 A1 | 4/2009 | Bagley et al. | |
| 2009/0126742 A1 | 5/2009 | Summer | |
| 2009/0319046 A1 | 12/2009 | Krespi et al. | |
| 2010/0037901 A1 | 2/2010 | Rousseau et al. | |
| 2010/0132719 A1 | 6/2010 | Jacobs et al. | |
| 2010/0158854 A1 | 6/2010 | Puisais | |
| 2010/0163056 A1 * | 7/2010 | Tschopp et al. | 128/848 |
| 2011/0100377 A1 * | 5/2011 | Weadock | A61F 5/566 128/848 |
| 2011/0166598 A1 | 7/2011 | Gonazles et al. | |
| 2011/0174315 A1 | 7/2011 | Zhang et al. | |
| 2011/0290258 A1 | 12/2011 | Pflueger et al. | |
| 2011/0308529 A1 | 12/2011 | Gillis et al. | |
| 2011/0308530 A1 | 12/2011 | Gillis et al. | |
| 2012/0017919 A1 | 1/2012 | Gillis | |
| 2012/0132214 A1 | 5/2012 | Gillis | |
| 2012/0138069 A1 | 6/2012 | Gillis et al. | |
| 2012/0143134 A1 | 6/2012 | Hollis et al. | |
| 2012/0180799 A1 | 7/2012 | Pflueger et al. | |
| 2013/0098374 A1 | 4/2013 | Gillis et al. | |

(56) References Cited

U.S. PATENT DOCUMENTS

| | | |
|---|---|---|
| 2013/0109910 A1 | 5/2013 | Alexander et al. |
| 2013/0233324 A1 | 9/2013 | Witt et al. |
| 2014/0000631 A1 | 1/2014 | Gillis et al. |
| 2014/0007885 A1 | 1/2014 | Gillis et al. |
| 2014/0014116 A1 | 1/2014 | Gillis et al. |
| 2015/0202074 A1 | 7/2015 | Gillis et al. |

FOREIGN PATENT DOCUMENTS

| | | |
|---|---|---|
| JP | 05-337126 A | 12/1993 |
| JP | 2604833 | 1/1997 |
| JP | 2001198147 | 7/2001 |
| JP | 2006507038 | 3/2006 |
| JP | 2007-97706 | 4/2007 |
| JP | 2007-512090 | 5/2007 |
| JP | 2007229485 | 9/2007 |
| JP | 2007525277 A | 9/2007 |
| WO | WO 97/18854 A1 | 5/1997 |
| WO | WO 99/00058 A1 | 1/1999 |
| WO | WO 00/66050 A1 | 11/2000 |
| WO | WO 01/89426 A1 | 11/2001 |
| WO | WO 02/13738 A1 | 2/2002 |
| WO | WO 02/076341 A2 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/055417 A1 | 7/2003 |
| WO | WO 03/065947 A1 | 8/2003 |
| WO | WO 2005/044158 A1 | 5/2005 |
| WO | WO 2006/012188 A1 | 2/2006 |
| WO | WO 2006/093533 A1 | 9/2006 |
| WO | WO 2006/101610 A2 | 9/2006 |
| WO | WO 2007/056583 A1 | 5/2007 |
| WO | WO 2007/070024 A2 | 6/2007 |
| WO | WO 2008/042058 A1 | 4/2008 |
| WO | WO 2008/097890 A2 | 8/2008 |
| WO | WO 2009/032625 A1 | 3/2009 |
| WO | WO 2010/028036 A1 | 3/2010 |
| WO | WO 2010/045546 A1 | 4/2010 |
| WO | WO 2010/051195 A1 | 5/2010 |

OTHER PUBLICATIONS

Gillis; U.S. Appl. No. 14/282,943 entitled "Partially erodable systems for treatment of obstructive sleep apnea," filed May 20, 2014.

DeRowe et al.; A minimally invasive technique for tongue base stabilation in obstructive sleep apnea; Operative Techniques in Otolaryngology-Head and Neck Surgery; 11(1); pp. 41-46; Mar. 2000.

Jeon et al.; Shape memory and nonostructure in poly(norbornyl-POSS) copolymers; Polym Int; vol. 49(5); pp. 453-457; May 2000.

Lui et al.; Thermomechanical characterization of a tailored series of shape memory polymers; J Applied Med Polymers; vol. 6/ No. 2; pp. 47-52; Sep. 2002.

Mather et al.; Strain recovery in POSS hybrid thermoplastics; Polymer Preprints; vol. 41, No. 1; pp. 528-529; (year of pub. sufficiently earlier than effective US filed and any foreign priority date) 2000.

Miller et al.; Role of the tongue base supension suture with the Repose System bone screw in multileval surgical management of obstructive sleep apnea; Otolaryngol Head Neck Surg.; 126(4); pp. 392-398; Apr. 2002.

Walker et al.; Palatal implants for snoring and sleep apnea; Operative Techniques in otolaryngology; 17(4); pp. 238-241; Dec. 2006.

Woodson et al.; Pharyngeal suspension suture with Repose bone screw for obstructive sleep apnea; Otolaryngol Head Neck Surg.; 122(3); pp. 395-401; Mar. 2000.

Rampersaud et al.; U.S. Appl. No. 14/340,324 entitled "Systems and methods for treatment of an airway disorder," filed Jul. 24, 2014.

Collins English Dictionary; "elastomer" (definition); Complete & Unabridged; 10th Edition; HarperCollins Publishers; May 11, 2015; retrieved from the internet (http://dictionary.reference.com/browse/elastomeric>).

* cited by examiner

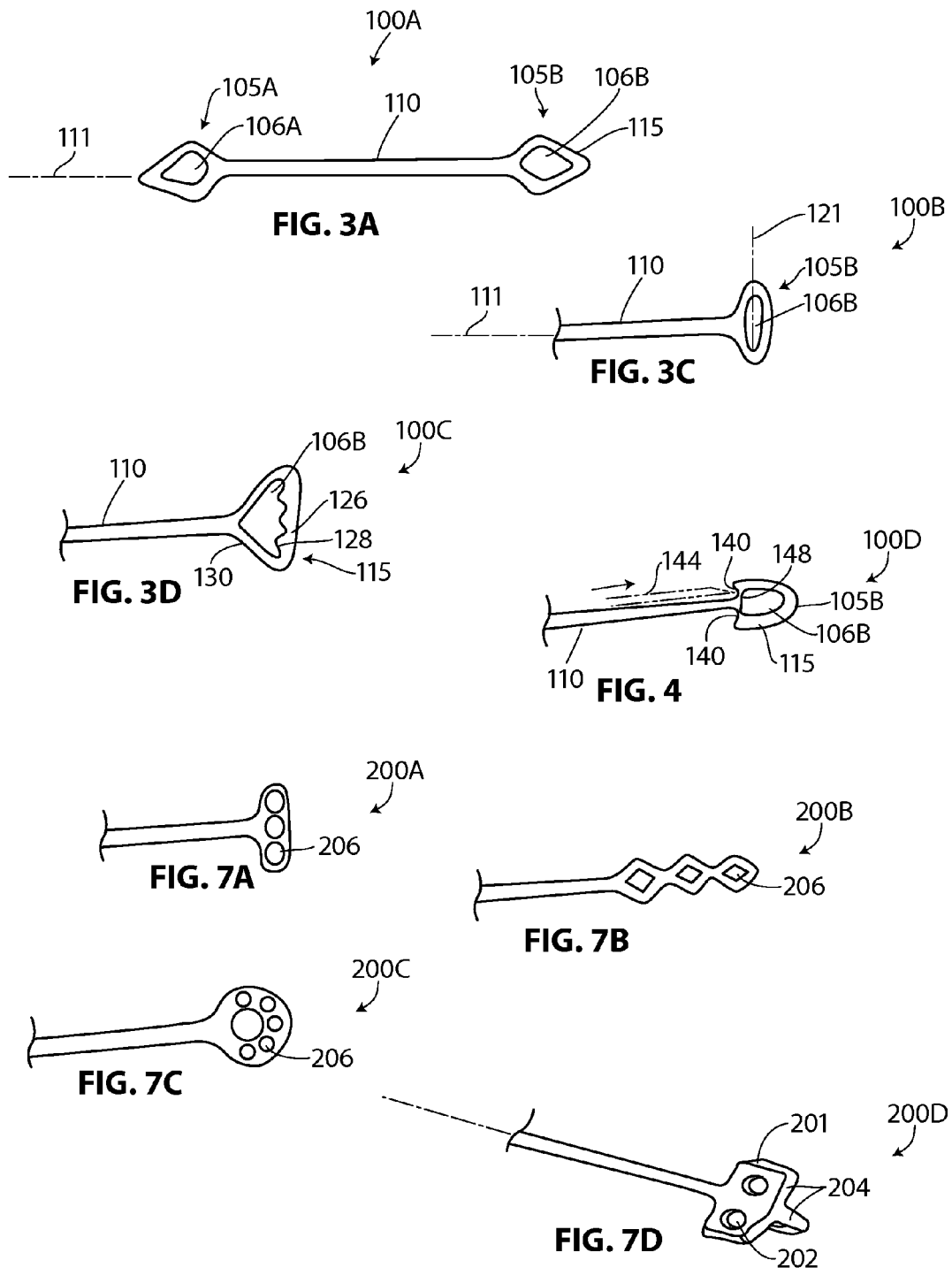

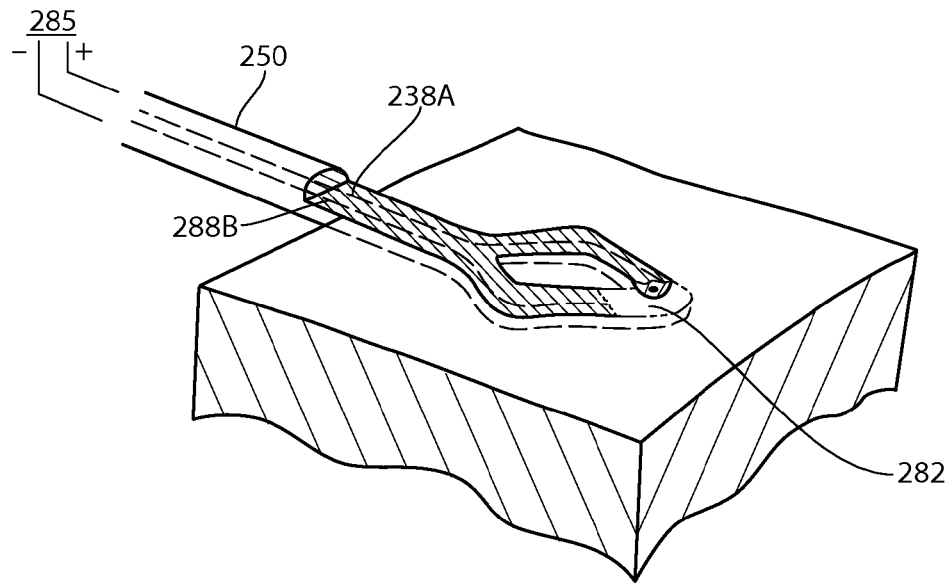
FIG. 12
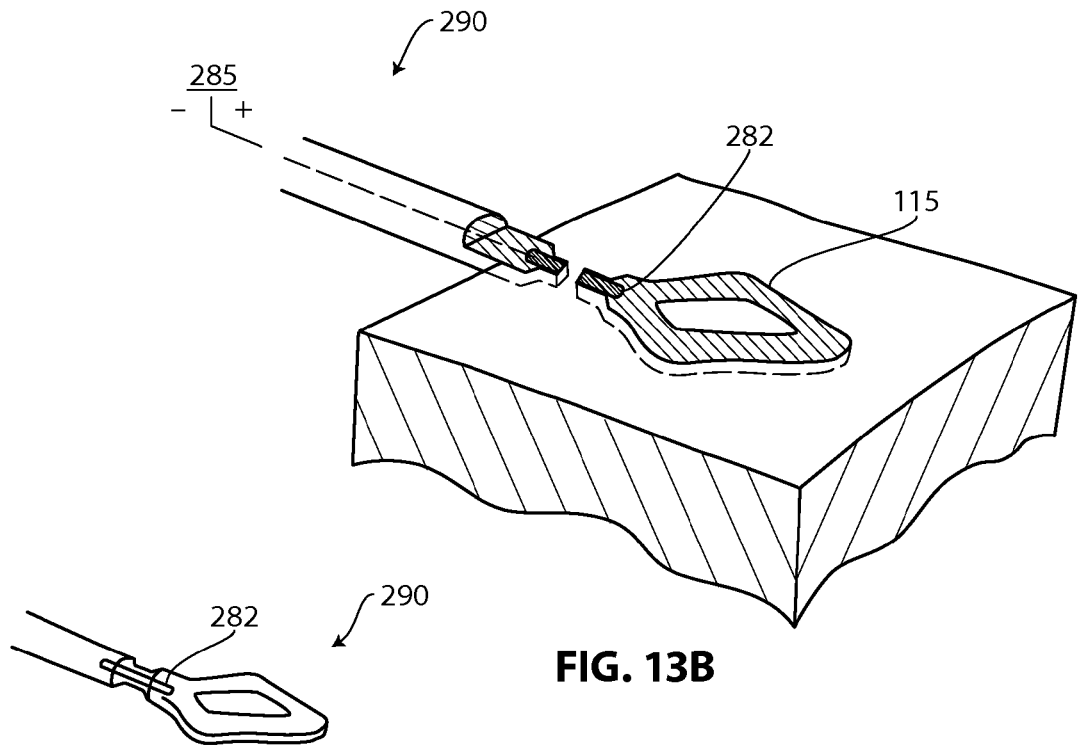
FIG. 13B
FIG. 13A

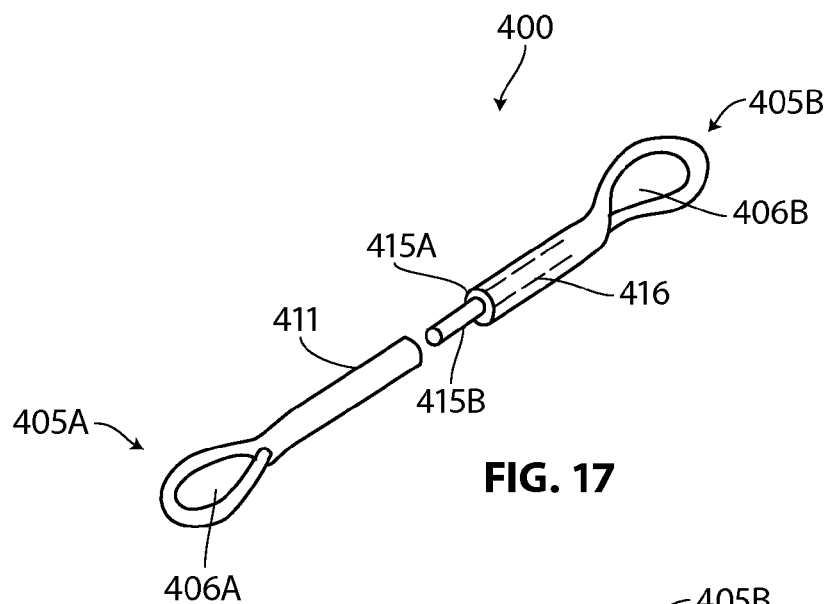
FIG. 17
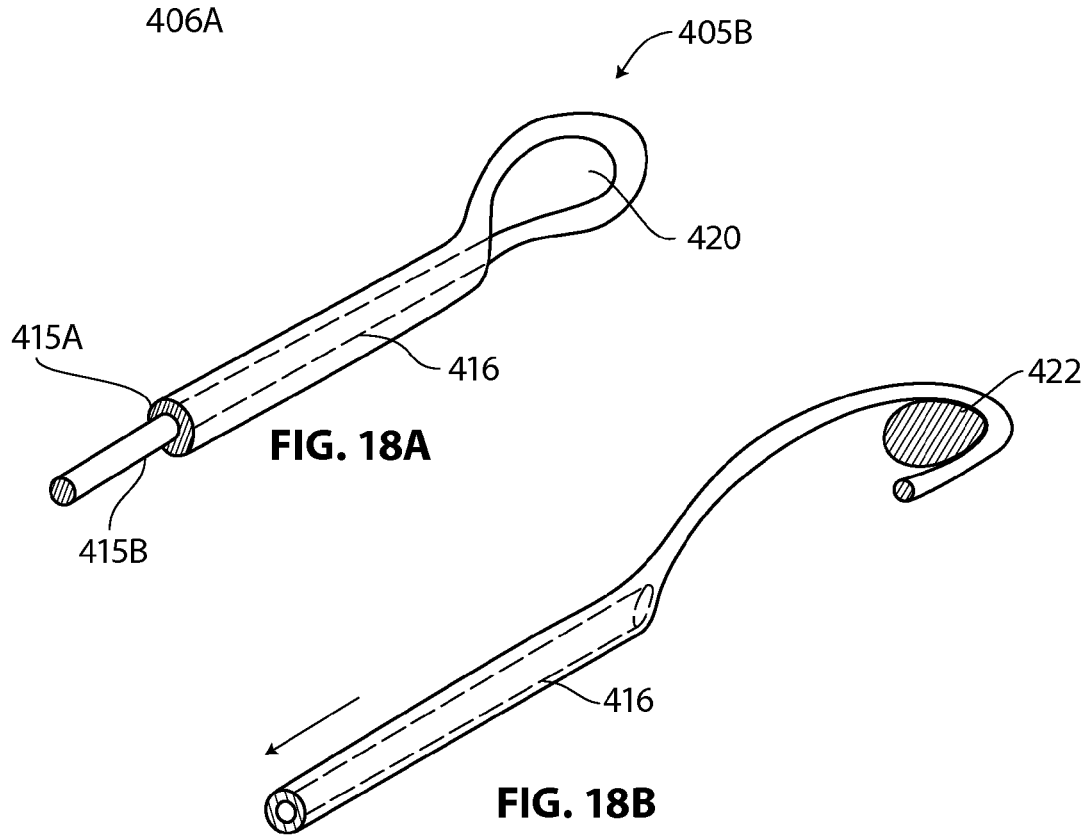
FIG. 18A
FIG. 18B

SYSTEMS AND METHODS FOR TREATMENT OF SLEEP APNEA

CROSS-REFERENCE TO RELATED APPLICATIONS

This application is a divisional of U.S. application Ser. No. 13/053,025, filed Mar. 21, 2011, now U.S. Pat. No. 8,776,799, which claims priority to: U.S. Provisional Application No. 61/315,835, filed Mar. 19, 2010; U.S. Provisional Application No. 61/315,838, filed Mar. 19, 2010; U.S. Provisional Application No. 61/347,348, filed May 21, 2010; U.S. Provisional Application No. 61/347,356, filed May 21, 2010; U.S. Provisional Application No. 61/367,707, filed Jul. 26, 2010; U.S. Provisional Application No. 61/418,238, filed Nov. 30, 2010; U.S. Provisional Application No. 61/419,690, filed Dec. 3, 2010, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The invention relates to the field of methods and devices for the treatment of obstructive sleep apnea, and more particularly to opening the airway of subjects with symptoms of obstructive sleep apnea.

BACKGROUND

Sleep apnea is defined as the cessation of breathing for ten seconds or longer during sleep. During normal sleep, the throat muscles relax and the airway narrows. During the sleep of a subject with obstructive sleep apnea (OSA), the upper airway narrows significantly more than normal, and during an apneic event, undergoes a complete collapse that stops airflow. In response to a lack of airflow, the subject is awakened at least to a degree sufficient to reinitiate breathing. Apneic events and the associated arousals can occur up to hundreds of times per night, and become highly disruptive of sleep. Obstructive sleep apnea is commonly but not exclusively associated with a heavy body type, a consequence of which is a narrowed oropharyngeal airway.

Cyclic oxygen desaturation and fragmented sleeping patterns lead to daytime sleepiness, the hallmark symptom of the disorder. Further consequences of sleep apnea may include chronic headaches and depression, as well as diminished facilities such as vigilance, concentration, memory, executive function, and physical dexterity. Ultimately, sleep apnea is highly correlated with increased mortality and life threatening co morbidities. Cardiology complications include hypertension, congestive heart failure, coronary artery disease, cardiac arrhythmias, and atrial fibrillation. OSA is a highly prevalent disease condition in the United States. An estimated 18 million Americans suffer from OSA to degrees that range from mild to severe, many of whom are undiagnosed, at least in part because the afflicted subjects are often unaware of their own condition.

Treatment of OSA usually begins with suggested lifestyle changes, including weight loss and attention to sleeping habits (such as sleep position and pillow position), or the use of oral appliances that can be worn at night, and help position the tongue away from the back of the airway. More aggressive physical interventions include the use of breathing assist systems that provide a positive pressure to the airway through a mask that the subject wears, and which is connected to a breathing machine. In some cases, pharmaceutical interventions can be helpful, but they generally are directed toward countering daytime sleepiness, and do not address the root cause. Some surgical interventions are available, such as nasal surgeries, tonsillectomy and/or adenoidectomy, reductions in the soft palate, uvula or the tongue base, or advancing the tongue base by an attachment to the mandible and pulling the base forward. These surgical approaches can be quite invasive and thus have a last-resort aspect to them, and further, simply do not reliably alleviate or cure the condition. There is a need for less invasive procedures that show promise for greater therapeutic reliability. There is additional need for the ability to reverse procedures or otherwise revise the procedure, thus allowing for the ability to reverse or otherwise revise the effects of the procedure due to side effects or other undesirable outcomes which may result from the procedure. Additionally, there is the need to do these procedural reversals or revisions in a manner that does not require excessive tissue cutting or invasiveness which can act as a deterrent for patients or physicians to perform such a revision procedure.

SUMMARY OF THE DISCLOSURE

The invention relates to a method of alleviating obstructive collapse of airway-forming tissues, and for devices with which to implement the method. Typical patients for whom the method and device may provide therapeutic benefit are those who suffer from obstructive sleep apnea. The method includes implanting a device at a site in the tissue and bioeroding the bioerodible portion of the device to change the shape of the device and to remodel the airway-forming tissue. The implanted device is sized and shaped to conform to the airway-forming tissue site in a manner compatible with normal physiological function of the site; and includes a resiliently deformable portion and a bioerodible portion. In, typical embodiments of the method, remodeling the airway-forming tissue results in the airway being unobstructed during sleep, and further, typically, the thus-unobstructed airway diminishes the frequency of apneic events. Remodeling may include reshaping or otherwise altering the position or conformation of airway associated tissue so that its tendency to collapse during sleep is diminished.

The airway is formed from various tissues along its length from the mouth to the lungs. Embodiments of the method include implanting a flexible implant, such as an elastomeric device, into any one or more of these tissues, including, for example, the soft palate, the tongue, generally the base of the tongue, and the pharyngeal walls, typically the posterior and lateral portions of the pharyngeal wall.

In some embodiments, the device is in a deformed shape when implanted, and a bioerodable portion erodes to thereby release a tensioned shape of the implant to apply retraction forces to the site.

With regard to the bioeroding of the bioerodible portion of the device, this may occur over a time span that ranges from days to months. In some embodiments, the bioeroding proceeds at a rate that correlates with the ratio of the biologically-exposed surface area of the bioerodible portion to the volume of the bioerodible portion.

In some embodiments of the method, the bioerosion occurs at a rate that is sufficiently slow for the tissue site to recover from the implanting prior to the device substantially changing shape. In some of these embodiments, the recovery of the tissue site includes a forming of fibrotic tissue around the device, which typically stabilizes the device in the site, and provides the device greater leverage with which to reform the shape of the implant site and its surrounding tissue. In some embodiments, after implanting, and as part of the healing response or recovery from the implantation wound, the newly formed fibrotic tissues infiltrates into holes, pores, or interstices in the device. In some embodiments of the method, a bioactive agent, previously incorporated into the bioerodible material, is released or eluted from the bioerodible portion of the device as it is eroding.

In another aspect of the methods described herein, a method of forming a device to alleviate obstructive collapse of an airway during sleep is provided. The method includes forming a resiliently deformable material into an initial shape that corresponds to the preferred shape of the device, the initial shape having a site for accommodating bioerodible material; changing the initial shape of the resiliently deformable material into a non-preferred shape that is sized and configured into an implantable shape that conforms to on airway-forming tissue site and is compatible with normal physiological function after implantation; and stabilizing the implantable shape by incorporating the bioerodible material into the accommodating site. In some of these method embodiments, changing the initial shape of the resiliently deformable material includes absorbing a force sufficient to remodel the airway as the force is transferred from the device into an implant site after implantation of the device. That level of force is further typically insufficient to remodel the airway to an extent that it is unable to move in a manner that allows substantially normal or acceptable physiological function of the airway.

As noted above, some aspects of the invention further provide a device for alleviating obstruction in an airway, such obstruction typically occurring during sleep. Embodiments of the device include an implantable device sized and shaped to conform to an airway-forming tissue site in a manner compatible with normal physiological function of the site, the device including a resiliently deformable portion and a bioerodible portion. In these embodiments, the resiliently deformable portion has a preferred shape that is constrained in a deformed shape by the bioerodible portion, and the device is configured to return toward the preferred shape of the resiliently deformable portion upon erosion of the bioerodible portion. In some embodiments, the preferred configuration is adapted to remodel the shape of the airway so as to provide a more open airway during sleep.

In typical embodiments of the device, the resiliently deformable portion may include any one or more of a metal or a polymer. In these embodiments, a resiliently deformable metal may include any one or more of stainless steel, spring steel, or superelastic nickel-titanium alloy, and a resiliently deformable polymer may include any one or more of silicon rubber, polyesters, polyurethanes, or polyolefins. In some embodiments, the bioerodible portion may include any one or more of polycaprolactone, polylactic acid, polyglycolic acid, polylactide coglycolide, polyglactin, poly-L-lactide, polyhydroxalkanoates, starch, cellulose, chitosan, or structural protein.

Some embodiments of the device include a portion adapted to engage the tissue into which it is implanted, and in some of these embodiments, the so-adapted portion includes a site for tissue in-growth, such in-growth serving to keep the device and tissue in close proximity, serving to promote implant site remodeling in a manner that conforms to the changing shape of the device. Finally, in some embodiments, the implantable device is configured with sufficient elasticity to allow normal physiological movement around an airway-forming tissue implant site when the device is implanted in the implant site.

In other embodiments, the adapted portion contains sites for tissue to link through the implant after implantation forming tissue plugs which thus form an attachment between the implant and the adjacent tissue without a corresponding adhesion of tissue to the implant. This type of arrangement can produce an implant that can effectively attach to and move tissue while remaining easily removable from the tissue. The tissue plugs can be formed by linking the implant around an encircled or surrounded mass of tissue or allowing tissue to heal through the implant thus forming the island of encircled or surrounded tissue. Implants can contain one or more surrounded masses of tissue allowing attachment to the adjacent tissue. In some embodiments, a proximal end of the implant is anchored to the patient's mandible and a distal end or ends of the implant is/are releasably anchored to one or more tissue plugs.

BRIEF DESCRIPTION OF THE DRAWINGS

FIG. 3A depicts an elongate implant component of a revisable OSA implant system, the implant having end portions with openings for growth of a tissue plug therethrough to secure the end portions in a treatment site.

FIG. 3C depicts another elongate implant embodiment similar to that of FIG. 3A.

FIG. 3D depicts another elongate implant embodiment.

FIG. 4 depicts another elongate implant corresponding to aspects of the invention.

FIG. 7A depicts another elongate implant corresponding to aspects of the invention.

FIG. 7B depicts another elongate implant embodiment.

FIG. 7C depicts another elongate implant embodiment.

FIG. 7D depicts another elongate implant embodiment with multiple openings in multiple planes.

FIG. 12 is a cut-away view depicting the implant of FIG. 11 in a tissue site after actuation of the sacrificial portion of the implant.

FIG. 13A depicts an alternative implant including an electrolytically sacrificial portion that can be sacrificed in response to a direct current.

FIG. 13B is a cut-away view depicting the implant of FIG. 13A in a tissue site after actuation of electrolytic connection portion of the implant.

FIG. 17 depicts an alternative revisable OSA implant.

FIGS. 18A and 18B illustrate an end portion of the revisable implant of FIG. 17.

DETAILED DESCRIPTION

A. Anatomy of the Pharynx

Figure 1:
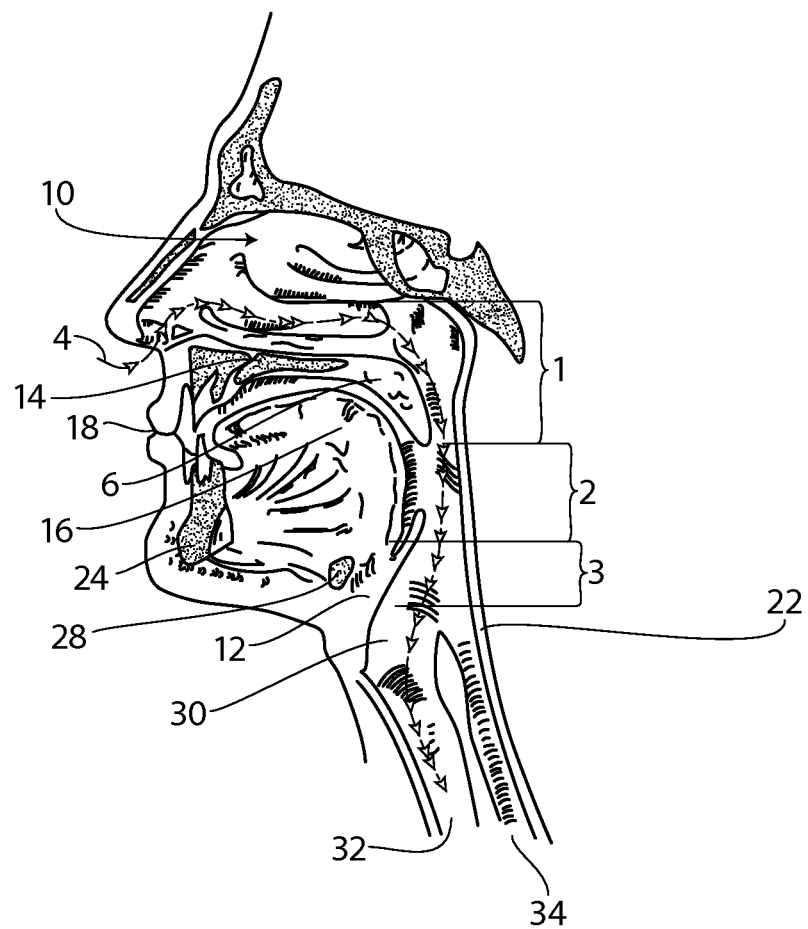
FIG. 1 provides an overview of the healthy human airway anatomy, with particular attention to the nasopharyngeal, oropharyngeal, and hypopharyngeal regions.
Figure 2A:
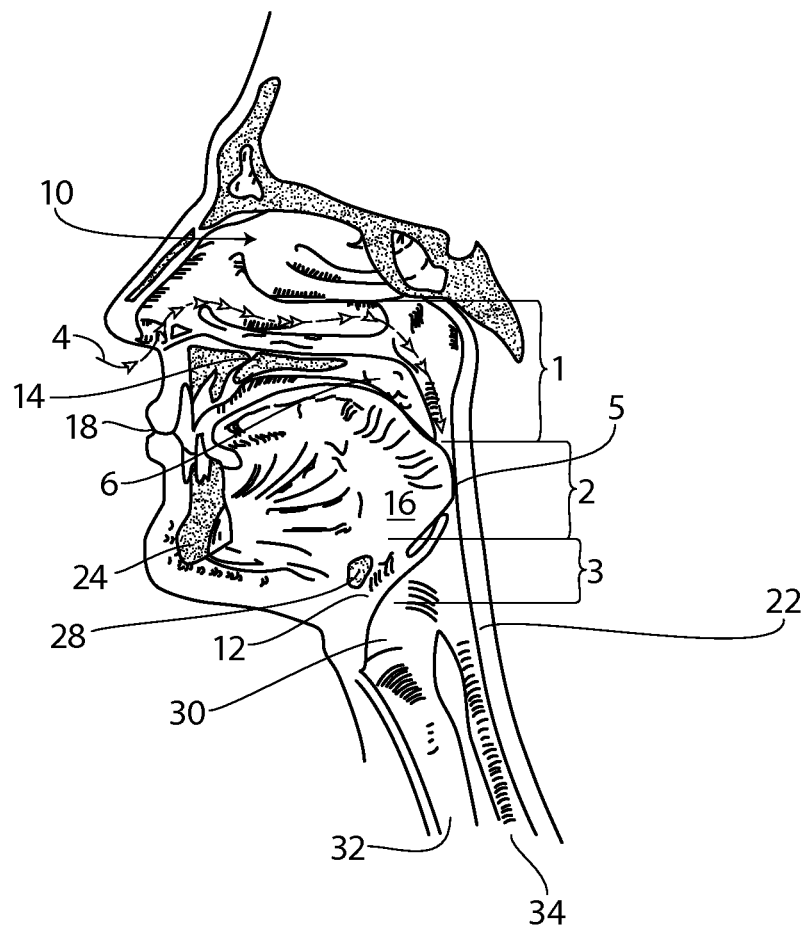
FIG. 2A provides a view of a compromised airway, with an occlusion in the oropharyngeal region due to posterior slippage of the base of the tongue.
Figure 2B:
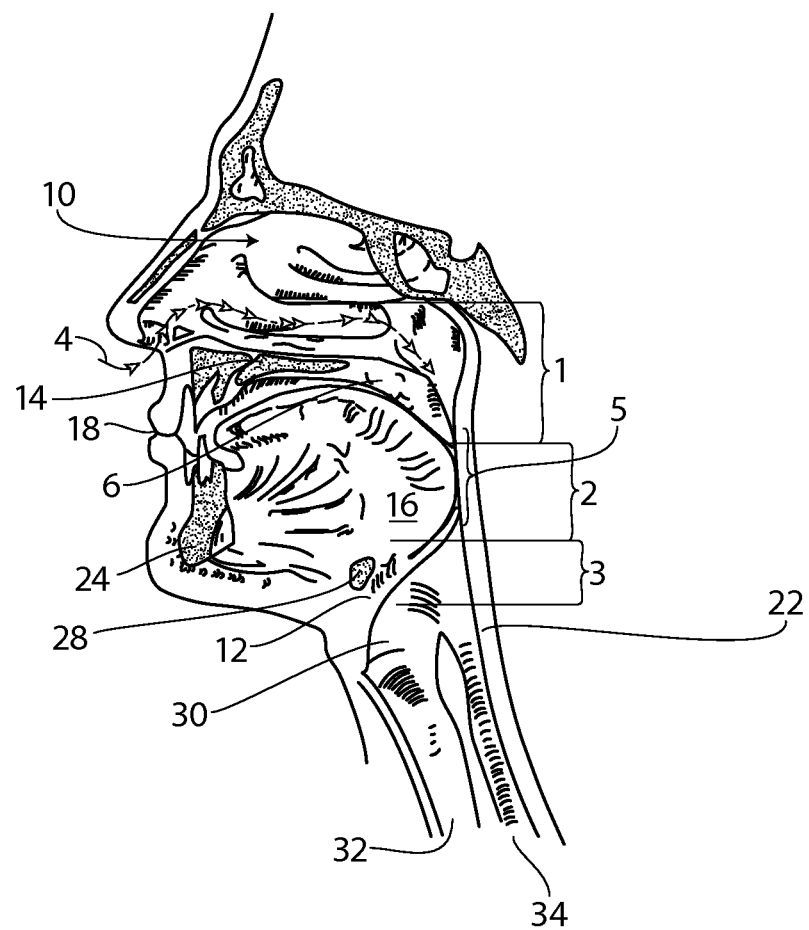
FIG. 2B provides a view of a compromised airway with palate closure.

FIG. 1 is a sagittal view of the structures that form the pharyngeal airway 4; some of these structures can become compromised under various conditions to the extent that they obstruct or occlude passage of air through the airway 4, and thus contribute to obstructive sleep apnea. The pharynx is divided, from superior to inferior, into the nasopharynx 1, the oropharynx 2 and the hypopharynx 3. Variations of FIG. 1 are provided in FIGS. 2A and 2B which depict airway obstruction sites 5 at various levels in the pharyngeal airway. FIG. 2A, for example, shows an occlusion 5 at the level of the oropharynx 2, where the base of the tongue 16 and a thickened posterior pharyngeal wall 22 have collapsed against each other. FIG. 2B provides a view of a compromised airway with palate closure. It is also possible for airway obstruction to occur at the level of the nasopharynx 1, where an elongated and/or floppy soft palate can collapse against a thickened posterior pharyngeal wall. Further, an obstruction can occur at the level of the hypopharynx 3, where both an elongated soft palate and a floppy epiglottis 12 can collapse against the pharyngeal wall 22.

With reference to FIGS. 1-2B, the nasopharynx 1 is the portion of the pharynx at the level of or above the soft palate 6. In the nasopharynx, a deviated nasal septum or enlarged nasal turbinates may occasionally contribute to upper airway resistance or blockage. Rarely, a nasal mass, such as a polyp, cyst or tumor may be a source of obstruction. The oropharynx 2 includes structures from the soft palate 6 to the upper border of the epiglottis 12 and includes the inferior surface of the hard palate 14, tongue 16, posterior pharyngeal wall 22 and the mandible 24. The mandible typically has a bone thickness of about 5 mm to about 10 mm anteriorly with similar thicknesses laterally. An obstruction in the oropharynx 2 may result when the tongue 16 is displaced posteriorly during sleep as a consequence of reduced muscle activity during deep or non-REM sleep. The displaced tongue 16 may push the soft palate 6 posteriorly and may seal off the nasopharynx 1 from the oropharynx 2. The tongue 16 may also contact the posterior pharyngeal wall 22, which causes further airway obstruction.

The hypopharynx 3 includes the region from the upper border of the epiglottis 12 to the inferior border of the cricoid cartilage. The hypopharynx 3 further includes the hyoid bone 28, a U-shaped, free-floating bone that does not articulate with any other bone. The hyoid hone 28 is attached to surrounding structures by various muscles and connective tissues. The hyoid bone 28 lies inferior to the tongue 16 and superior to the thyroid cartilage 30. A thyrohyoid membrane and a thyrohyoid muscle attach to the inferior border of the hyoid 28 and the superior border of the thyroid cartilage 30. The epiglottis 12 is infero-posterior to the hyoid bone 28 and attaches to the hyoid bone by a median hyoepiglottic ligament. The hyoid boric attaches anteriorly to the infero-posterior aspect of the mandible 24 by the geniohyoid muscle. Below the hypopharynx 3, the trachea 32 and esophagus 34 are also shown.

B. Revisable OSA Implants

FIG. 3A depicts a first component in an exemplary embodiment of a kit or system that provides revisable implants for treating airway disorders or obstructive sleep apnea (OSA). The second component of the exemplary kit is an introducer for insertion into a treatment site as is known in the art and co-pending applications. In FIG. 3A, an elongate device or implant body 100A has first and second end portions 105A and 105B with through-openings 106A and 106B therein. The medial portion 110 of the implant body 100A extends along axis 111 and comprises a biocompatible elastomeric material such as a silicone. The mean cross-section of the medial body portion 110 can range from 1 to 10 mm$^2$ and can be round, oval, flat, polygonal or other suitable shapes. In some embodiments, the elastic modulus of the medial portion can range from 0.5 to 10 MPA and is configured for implanting in the patient's airway tissue in a releasable, tensioned position, as described in co-pending U.S. patent application Ser. No. 11/969,201 which is incorporated herein by this reference.

Figure 3B:
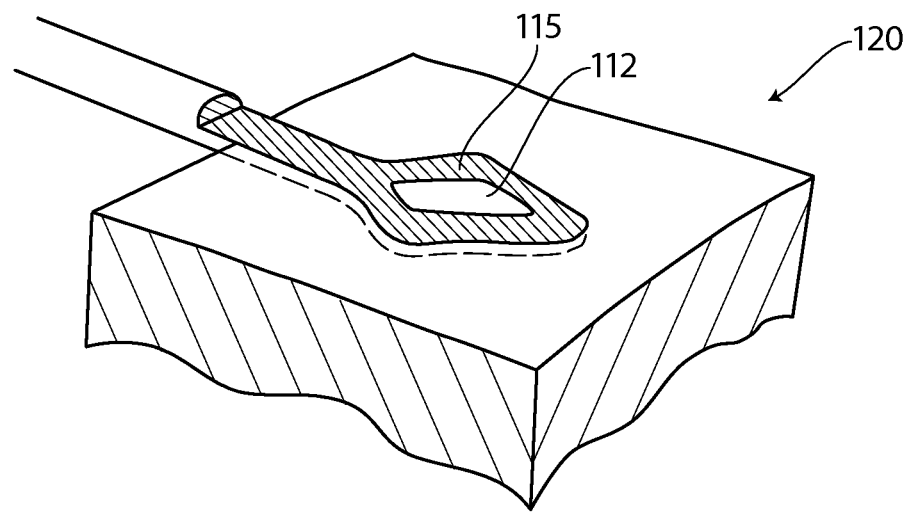
FIG. 3B is a cut-away view of an end portion of the implant of FIG. 3A in a tissue site.

Referring to FIGS. 3A and 3B, it can be seen that through-openings 106A and 106B in the implant body 100A are configured for growth of a tissue plug 112 through the opening to thereby secure the first and second end portions 105A and 105B in a selected tissue, site. The cut-away view of FIG. 3B schematically illustrates that a tissue plug 112 that grows through the opening is thus surrounded or encircled by an encircling body portion 115 of the implant. The encircling body portion 115 comprises a small cross-section element that can be cut, severed, sacrificed, decoupled, or dissolved to disengage the implant from a tissue site 120 as will be described below. The element can be a polymer or other material. In other embodiments described below, the tissue plug 112 can be cut or severed to disengage the implant from the tissue site 120. In one embodiment, the mean cross-section of the tissue plug 112, and thus the dimension across an opening 106A or 106B, can range from about 0.5 mm to 10 mm or more. The openings 106A or 106B can have a round shape in plan view or any other plan shape. The end portions 105A and 105B can have similar or dissimilar configurations, for example an implant configured for treatment of a patient's tongue may have a substantially larger end portion and opening 106B for the base of the tongue and a smaller end portion near the mandible.

FIG. 3C illustrates another implant body 100B with an end portion 105B having an elongated opening 106B through which tissue will grow to form a tissue plug to secure the end portion in the site. For example, the implant body 100B of FIG. 3C has an opening 106B with a primary axis 121 and larger dimension that extends generally orthogonal to the axis 111 of medial portion 110 of the implant body. In use, the greater dimension of the tissue plug will better resist the retraction forces applied to tissue by the elastomeric medial portion 110 of the implant aligned with axis 111.

FIG. 3D depicts another embodiment 100C of a revisable implant for treating an airway disorder that is similar to that of FIG. 3C except the end portion 105B has a through-opening 106B with a terminal part 126 of encircling portion 115 configured with irregular shaped surface features 128 that can interface with the tissue plug that grows through opening 106B. The surface features can comprise undulations, textures, protrusions, bumps and the like that can assist in maintaining the end portion in a fixed position when under the tensioning or retraction forces applied by the medial portion 110 of the implant body 100C. In the implant body 100C of FIG. 3D, the end portion 105B also can have an encircling element 115 that includes a proximal portion 130 of a lower modulus material similar to the modulus of medial portion 110 and the terminal part 126 having a higher modulus to prevent its deformation under tensioning forces.

FIG. 4 depicts another embodiment 100D of a revisable implant that is similar to previous embodiments except that at least one end portion 105B includes an indent feature 140 in the proximal-facing aspect of the encircling portion 115 wherein the indent feature 140 is adapted to direct and receive a cutting blade or edge 144 (phantom view) of a cutting tool for cutting the encircling portion of the implant body to allow its removal from the treatment site. As will be described below (with reference to FIG. 5B), a cutting tool 145 can be advanced along the medial portion 110 of the implant to sever the end portion, which then will allow the entire implant to be withdrawn from the implant site. In another aspect of the invention, the indent feature 140 in the encircling portion 115 can direct the cutting edge 144 to a reduced cross section portion 148 that will require limited force to cut the polymer element with the cutting edge 144.

Figure 5A:
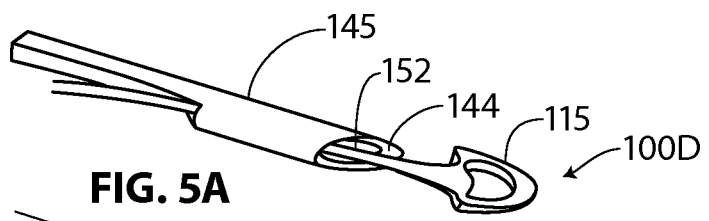
FIG. 5A depicts a second component of a revisable OSA implant system, the second component comprising a cutting tool.
Figure 5B:
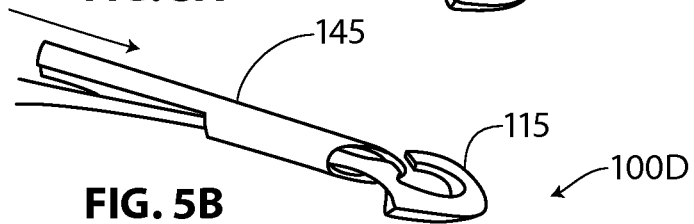
FIG. 5B depicts the cutting tool of FIG. 5A in a method of use.

FIGS. 5A and 5B illustrate a second component of an exemplary kit of a revisable OSA implant system wherein the tool 145 comprises an elongate member with a distal cutting edge 144. One tool embodiment has a passageway 152 extending therethrough for receiving the elongate implant body 100D. In using this tool 145, a first end of the implant body would be freed from tissue or cut and then threaded through the passageway 152. Thereafter, as depicted in FIG. 5B, the tool 145 can be advanced distally while holding the proximal end of the implant to cause the cutting edge 144 to cut across the encircling portion 115. In FIG. 5B, it can be understood how the indent feature 140 and reduced cross section portion 148 (see FIG. 4) direct the cutting edge 144 to easily cut the element to thus release the implant from encircling the tissue plug 112 (cf. FIG. 3B). The tool 145 can be a rigid or semi-rigid member such as a hypotube with a sharpened end. The tool also can be a deflectable, articulatable or steerable member as is known in the art. In another embodiment, the tool can be a flexible plastic material with a blade insert to provide the cutting edge 144. Referring to FIGS. 5B and 3B, it can be understood that the cut end is flexible and can be pulled from around the tissue plug to extract the implant from the site 120 (see FIG. 3B).

Figure 6:
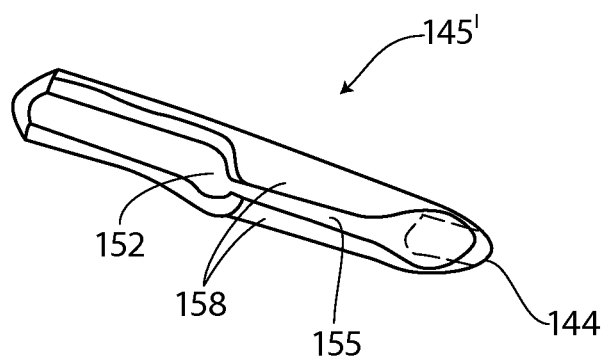
FIG. 6 depicts an alternative cutting tool similar to that of FIGS. 5A-5B.

FIG. 6 illustrates another second tool component of a revisable implant system wherein the tool 145' again comprises an elongate member with a distal cutting edge 144. In one embodiment, the tool end includes a longitudinal gap 155 along a side of passageway 152 to thus allow the tool to be inserted over medial portion 110 of an implant body to then advance and cut the implant as depicted schematically in FIGS. 5A-5B. The tool end as shown in FIG. 6 can comprise a polymer member with flexible elements 158 on either side of gap 155 to allow gap 155 to flex open when the device is being inserted over the implant. As depicted, distal cutting edge 144 may comprise a metal blade insert 160 molded into a polymer member.

FIGS. 7A-7C illustrate other embodiments of implants 200A, 200B and 200C that each has a plurality of through-openings 206 in various configurations. In these embodiments, the ends are flat or planar with the openings therein. Thus, in use, there will be a plurality of tissue plugs that grow through the openings 206 to secure the implant ends in the tissue site.

FIG. 7D illustrates another embodiment of implant 200D that has a non-planar end 201 with a plurality of through-openings 202. In one embodiment, the ends have a plurality of elements 204 that extend in different radial angles relative to the axis 111 of the implant with each such element 204 having one or more openings therein.

Figure 7E:
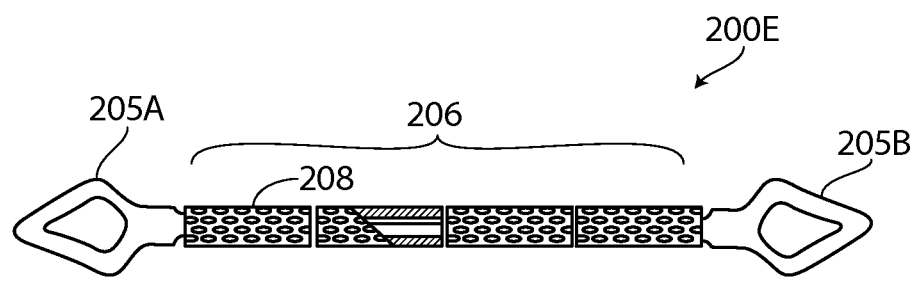
FIG. 7E is a partially cut-away view that depicts an OSA implant with an elastomeric portion that is configured for being releasably maintained in a tensioned or non-repose condition by a magnesium or magnesium alloy biodissolvable material or element.

FIG. 7E illustrates an implant body 200E with ends 205A and 205B and medial portion 206 that comprises an axially-stretched and tensioned elastomeric material. The medial portion 206 is releasably and temporarily maintained in the axially-stretched non-repose condition by a biodissolvable portion, such as of magnesium or magnesium alloy, indicated at 208. In this embodiment, the biodissolvable portion can comprise a tubular member with a foil-like wall or thin-wall, a plurality of thin-wall tube segments, or one or more windings or braids of biodissolvable material. The thin-wall material can be perforated as shown in FIG. 7E. The thin-wall biodissolvable material, or the biodissolvable filament of a winding or braid, can be very fine and adapted to dissolve, erode and/or absorb into the body with selected time interval ranging from about 2 weeks to 52 weeks. In another embodiment, the biodissolvable portion can be disposed in an interior portion of the implant body, in a linear or helical configuration.

Embodiments of the invention include methods for opening a collapsed or obstructed airway with devices that can be implanted into various tissues that form the airway. Embodiments of the devices include resiliently deformable materials and bioerodible materials. The deformable portion of devices, when first formed, is formed into a preferred shape which is then subsequently deformed, and stabilized in that deformed shape by incorporation or application of bioerodible materials to create a device in its implantable form. Once implanted into a tissue site, and thus exposed to an aqueous environment and subject to cellular and enzymatic action, the bioerodible portions of the device erode, thereby allowing the deformable portion of the device to return toward the preferred form. Embodiments of the method, in their simplest form, thus include implanting a device, the bioerodible portion of the device bioeroding, the device changing shape as a consequence of the bioeroding, and the tissue remodeling in accordance with the force being exerted by the shape changing of the device.

Referring again to FIG. 7E, in operation exemplary device 200E may be implanted into an airway-interface tissue site, such as a patient's tongue. Device 200E is configured with appropriate characteristics, such as its dimensions and flexibility, to be compatible with normal physiological function of the tissue site, such as swallowing and speech. When first implanted, biodissolvable portions 208 maintain medial portion 206 in a stretched configuration. As shown, first and second openings extend through first and second implant ends 205A and 205B, respectively. As the tissue adjacent the implant heals after device 200E is implanted, these openings allow tissue plugs to grow through them, permitting each of the first and second implant ends to surround a tissue plug that forms. This allows the ends of implant 200E to become anchored in the tissue site before portions 208 dissolve and release the stored tension between ends 205A and 205B. Once biodissolvable portions 208 have dissolved and pre-stretched medial portion 206 applies tension between the tissue plugs, the base of the tongue, for example, is drawn in an anterior direction to open a collapsed or obstructed airway. In some embodiments (not shown), the ends of the device may be configured to encircle the tissue plugs upon implantation, without requiring healing time for the tissue plugs to grow through the openings in the ends of the device. Further details of such devices are provided in U.S. provisional application 61/347,356, and further examples of implantation procedures are provided in U.S. application Ser. Nos. 11/969,201 and 12/937,564.

Figure 8A:
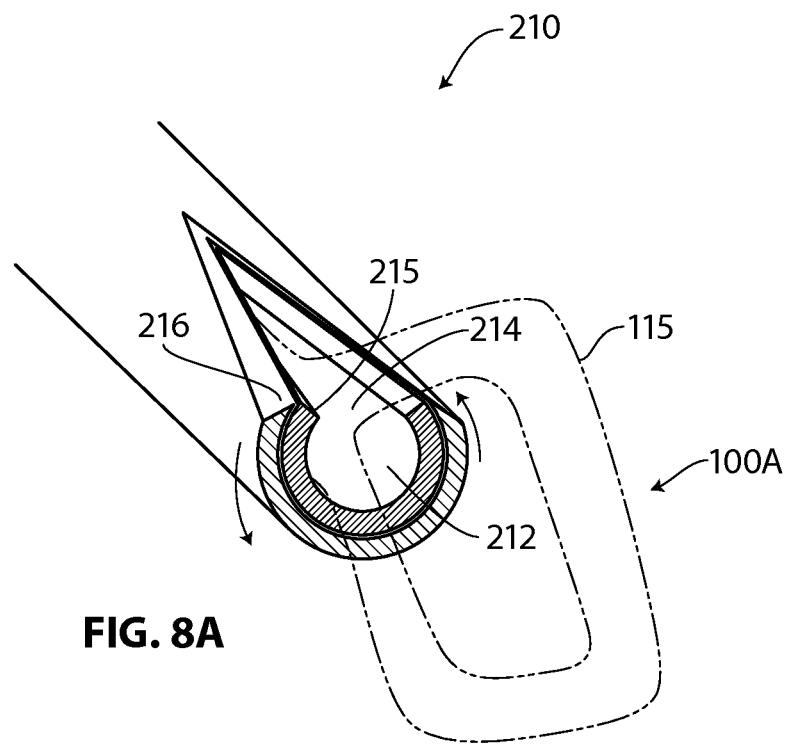
FIG. 8A depicts the working end of another embodiment of a cutting tool for cutting a portion of an implant in situ.
Figure 8B:
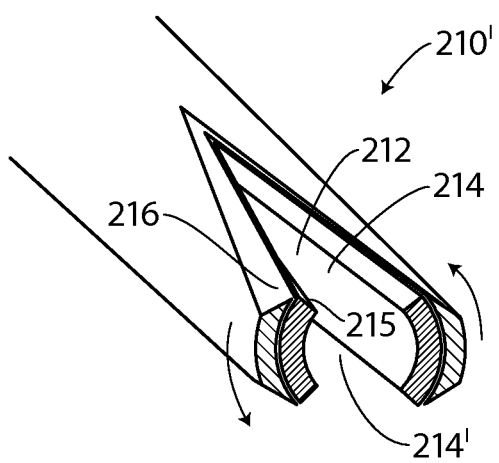
FIG. 8B depicts another embodiment of a cutting tool for cutting an implant in a revision procedure.

FIG. 8A depicts the working end 210 of an elongated tool that is adapted for cutting an end portion of an implant for its removal, for example an implant of FIGS. 3A-3D, 4, or 7A-7D. The tool functions similar to that of FIGS. 5A and 6, wherein the tool has a central bore 212 that receives the elongate medial portion of an implant body. As can be seen in FIG. 8A, the working end 210 includes two concentric hypotubes with a notch 214 therein to push over an end portion 115 of implant 100A of FIG. 3A, for example. The physician can counter-rotate the hypotubes from a proximal handle end wherein blade edges 215 and 216 of the working end function as a scissors mechanism to cut the implant body. Thereafter, the implant can be easily removed from the treatment site. FIG. 8B illustrates another working end 210' of a similar cutting tool that has opposing notches 214 and 214' that can receive a implant body portion and blade edges 215 and 216 can be rotated or pivoted to cut the implant.

Figure 9:
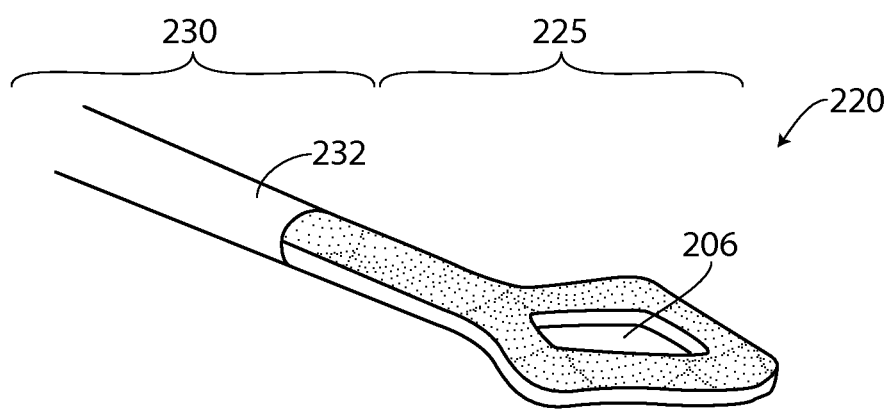
FIG. 9 depicts another implant with a medial portion having a surface configured for low adhesive energy.

FIG. 9 illustrates another embodiment of implant 220 that is similar to any previous embodiment except depicting a difference in surface characteristics of the implant. The end or encircling portion 225 may have smooth or slightly textured surface features and the medial portion 230 may comprise a highly lubricious surface, such as an elastomeric material having an ultra-hydrophobic surface 232 to allow for slippage of the tissue against the implant during use. Thus, a method of the invention comprises implanting a device in airway-interface tissue, securing first and second implant end portions in the tissue by permitting a tissue growth through at least one opening in an end portion, and allowing an elastomeric portion of the implant to apply retraction forces to alleviate tissue obstruction of the airway wherein an ultahydrophobic surface of the implant prevents tissue adhesion to said surface. Ultrahydrophobic surfaces can be provided in a biocompatible polymer, as is known in the art.

In another aspect of the invention, referring to FIG. 9, the elongate implant body is configured for implanting in an airway-interface and at least a portion of a body surface has a wetting contact angle greater than 70°, to prevent tissue adhesion and to allow tissue slippage. In other embodiments, at least a portion of a body surface has a wetting contact angle greater than 85°, or greater than 100°.

In another aspect of the invention, still referring to FIG. 9, the elongate implant body is configured for implanting in an airway-interface and at least a portion of a body surface has an adhesive energy of less than 100 dynes/cm, less than 75 dynes/cm or less than 50 dynes/cm.

Figure 10:
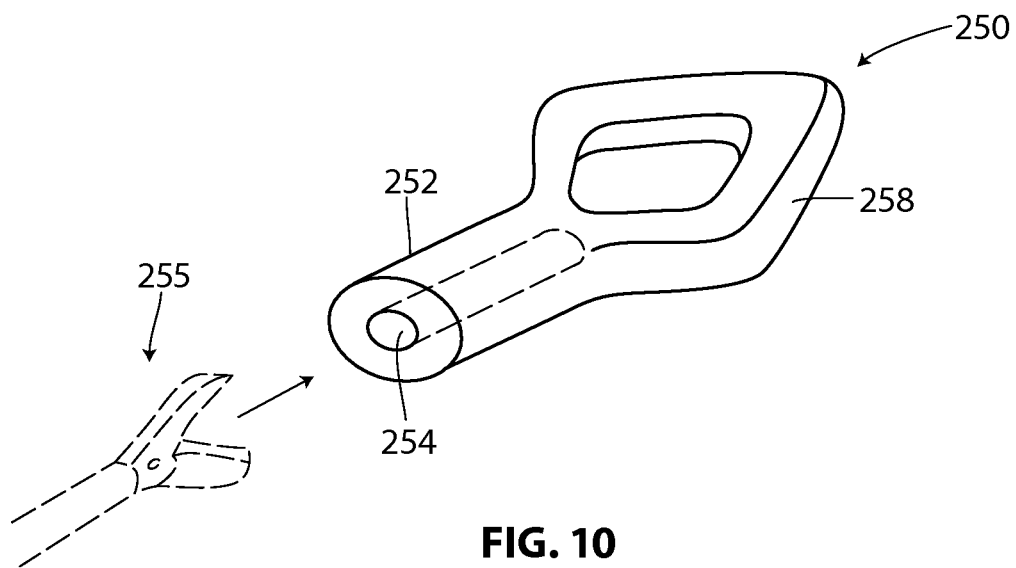
FIG. 10 depicts another elongate implant corresponding to aspects of the invention.

FIG. 10 illustrates another embodiment of revisable OSA implant 250 similar to previous embodiments except the medial portion 252 includes a passageway 254 configured for extending a cutting tool 255 through the passageway for cutting a distal end portion 258 of the implant. The passageway 254 can be accessed by an access opening in the opposing end (not shown) that can be identified by imaging of a marker, visual observation of a marker, by a left-in place guidewire or other suitable means or mechanism. The cutting tool 255 can comprise a scissor member, an extendable blade that is extendable from a blunt-tipped tool, any distal or proximally-facing blade, and/or any type of thermal energy emitter adapted for cutting the implant end 258.

Figure 11:
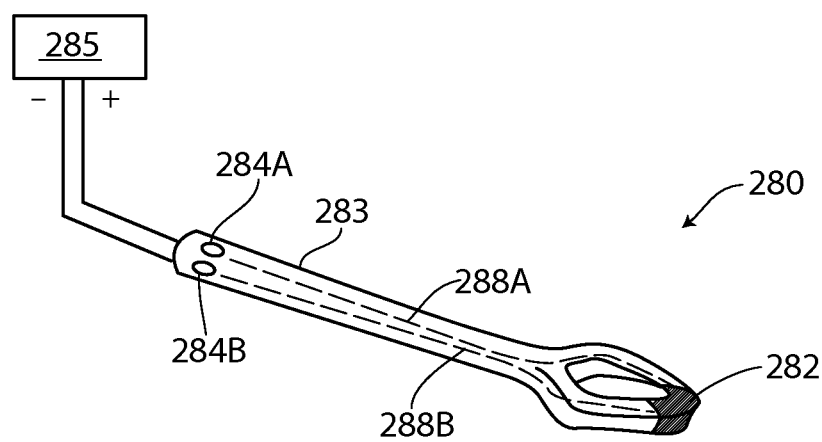
FIG. 11 depicts another implant corresponding to aspects of the invention including a sacrificial portion that can be sacrificed in response to an external stimulus.

FIG. 11 illustrates another embodiment of revisable OSA implant 280 that has a sacrificial portion indicated at 282 that can be severed or sacrificed by an external stimulus. In one embodiment, a medial portion 283 of the implant includes electrical contacts or extending leads 284A and 284B that can be detachably coupled to an electrical source 285. In FIG. 11, the implant body comprises an elastomeric material as described above and the sacrificial portion 282 comprises a conductively doped polymer portion that acts as a fuse when subject to a very short burst of high voltage RF current. Opposing sides or aspects of the sacrificial portion 282 are coupled to electrical leads 288A and 288B that are embedded or molded into the implant. The use of such doped polymers for a fuse-effect for detachment of endovascular medical implants is disclosed in U.S. Pat. No. 6,458,127 to Truckai et al and issued Oct. 1, 2002, which is incorporated herein by reference. Similar doped polymers can be used in the revisable OSA implant of FIG. 11.

FIG. 12 illustrates a method of using the OSA implant 280 of FIG. 11, and more particularly for revising the treatment. FIG. 12 depicts that an RF current from source 285 has been delivered to melt, sever and sacrifice portion 282 of the implant thus allowing extraction of the implant from around the tissue plug.

FIGS. 13A and 13B illustrate another embodiment of revisable OSA implant 290 that has a sacrificial portion indicated at 282 in a medial portion of the implant that can be actuated and sacrificed by the external stimulus which then leaves the encircling portion 115 of the implant in place. The left-in-place portion of the implant can be used as an anchor for subsequent implants. In one embodiment as in FIGS. 13A-13B, the sacrificial portion 282 can comprise an electrolytic wire that can be sacrificed over a short time interval by direct current as is known in the art. Such electrolytic wire for detachment of embolic coil implants are known in the field of aneurysm implants and treatments.

While FIGS. 11-13B show OSA implants with two forms of sacrificial portions, it should be appreciated that similar implants can have sacrificial portions that are cut, severed or sacrificed by any external stimulus such as RF current, DC current, light energy, inductive heating etc. and may fall within the scope of the invention.

Figure 14:
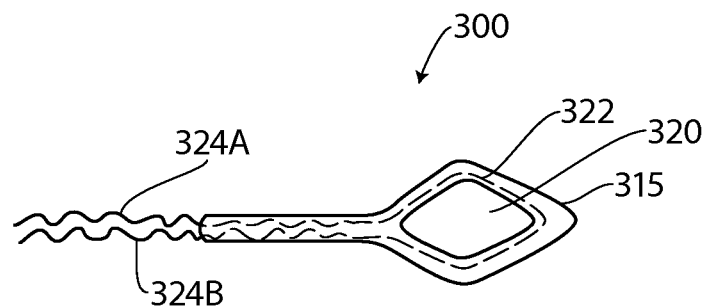
FIG. 14 depicts an end portion of an alternative revisable implant including a cut wire for cutting a tissue plug.
Figure 15:
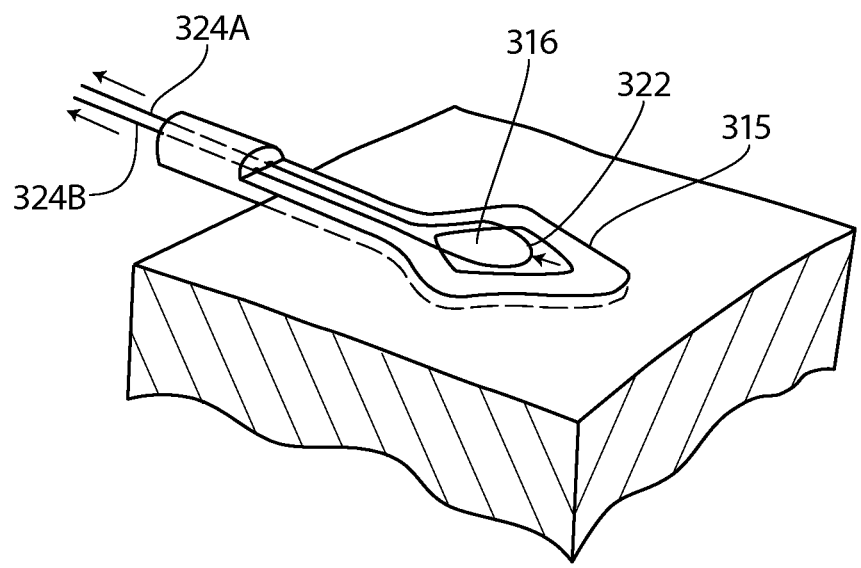
FIG. 15 is a cut-away view depicting the implant of FIG. 14 in a tissue site in the process of actuating the cut wire.

FIGS. 14 and 15 illustrate another embodiment of revisable OSA implant 300 that again includes at least one end with an encircling portion indicated at 315 that encircles or surrounds a tissue plug 316 that grows through an opening 320. In one embodiment, the implant carries a cut wire 322 that extends in a loop with first and second wire ends 324A and 324B extending through one or more passageways in the implant. The cut wire 322 can be embedded in the surface of the implant surrounding the opening 320. As can be seen in FIG. 15, the looped cut wire 322 can be pulled proximally to cut the tissue plug 316 which then will free the implant from its attachment. In FIG. 14, it can be seen that the cut wire ends 324A and 324B can have a serpentine configuration in the medial portion of the implant so as to not interfere with the tensioning and relaxation of the elastomeric medial implant portion during its use. When the cut wire is accessed and pulled relative to the implant 300, the tissue plug 316 can be cut. It should be appreciated that other tools (not shown) may be used to stabilize the implant when actuating the cut wire as in FIG. 15. The cut wire 322 can be any form of fine wire, or abrasive wire or a resistively heated wire coupled to an electrical source (not shown).

Figure 16:
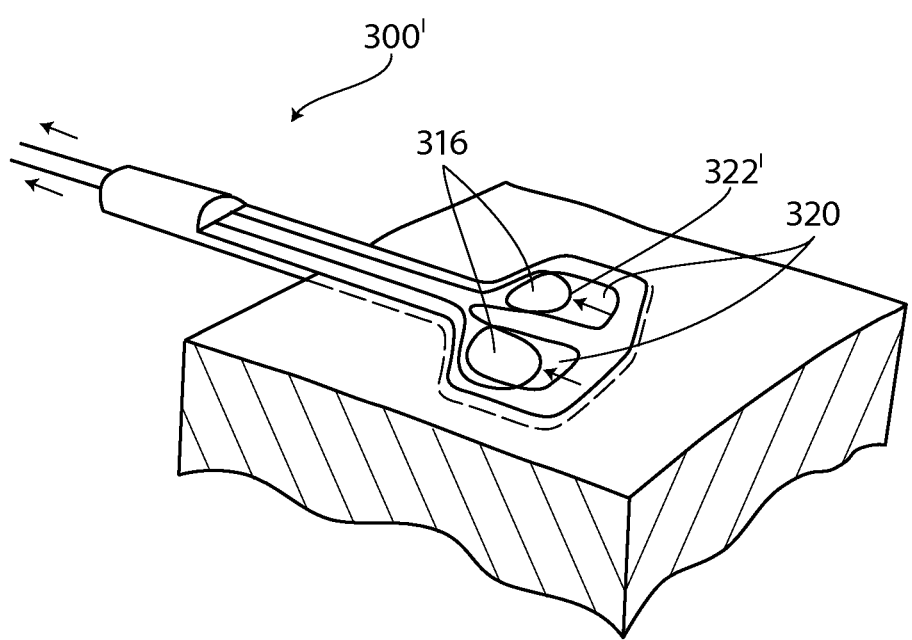
FIG. 16 depicts an end portion of an alternative revisable implant including a cut wire for cutting a plurality of tissue plugs.

FIG. 16 depicts another revisable USA implant 300' that is similar to that of FIGS. 14-15 with the cut wire 322' configured to cut a plurality of tissue plugs 316 that have grown through openings 320 within an encircling end portion of the implant body.

FIG. 17 depicts another OSA implant 400 that is adapted for revision as previous implants and systems wherein the elongate device or implant body has first and second end portions 405A and 405B with through-openings 406A and 406B therein. The medial portion 411 of implant body 400 extends about an axis and comprises a biocompatible elastomeric material such as a silicone. In this embodiment, the medial portion comprises first and second extending portions 415A and 415B wherein one such portion can be nested in a passageway 416 of the other portion and then form proximal and distal loops or encircling end portions that define openings 406A and 406B for receiving tissue plugs therein. As can be understood from FIGS. 17 and 18A, both the extending portions 415A and 415B comprise an elastomeric material and thus combine to provide the desired retraction forces of the OSA implant.

Referring to FIGS. 18A and 18B it can be seen that if the second extending portion 415B is cut in a medial or proximal aspect of the implant, or if both the first and second extending portions 415A and 415B are cut in a proximal or medial aspect, then a proximal aspect of the first or outer extending portion 415A can be pulled in the proximal direction and the cut second extending portion 415B then will snake out of the path around the tissue plug 422. Thus, the implant can be cut in a proximal or medial aspect and can be withdrawn from the treatment site from a remote access location.

Figure 19:
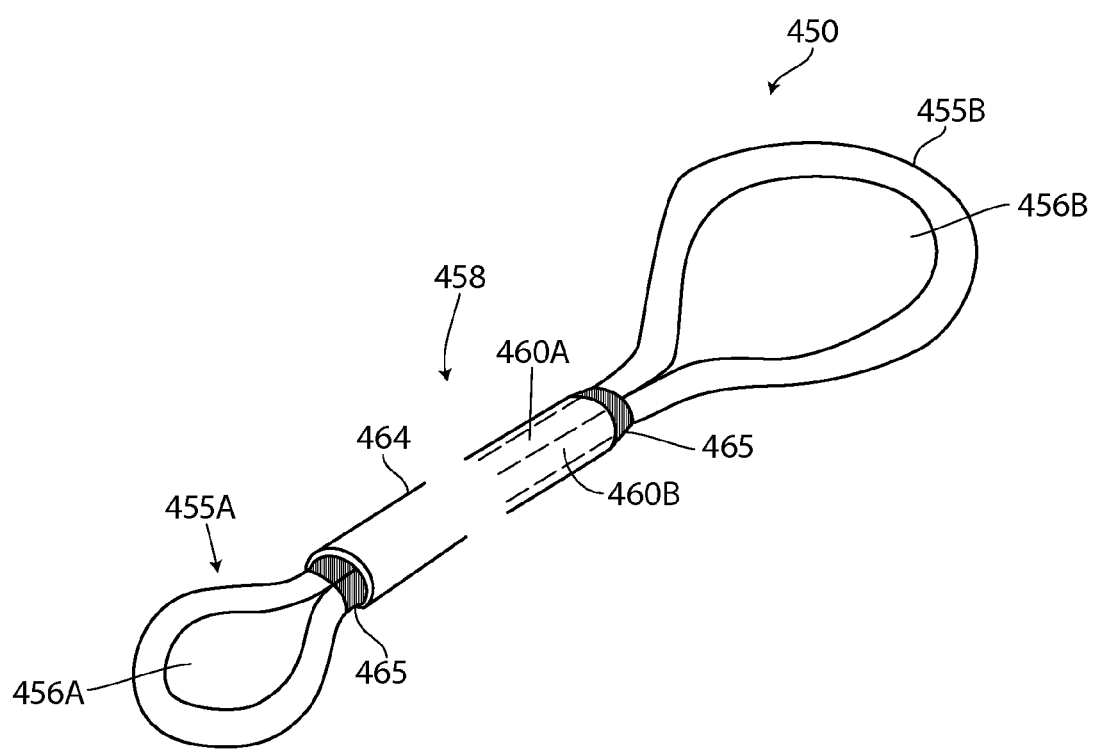
FIG. 19 depicts an alternative revisable OSA implant.

FIG. 19 depicts another OSA implant 450 that is adapted for a revision procedure and comprises an elongate implant body with first and second end portions 455A and 455B with through-openings 456A and 456B therein. This embodiment is similar to that of FIG. 17 in that medial portion 458 includes extending portions 460A and 460B comprising an elastomeric material that combine to provide the desired retraction forces of the OSA implant. The extending portions 460A and 460B are carried in a thin elastomeric sleeve 464 that has tear-away portions 465 about its ends to prevent tissue ingrowth into the passageway in the sleeve. It can be understood that by cutting the medial portion of the implant, and then pulling on an end of an extending portion 460A or 460B will cause the other free end of the implant to snake around the tissue plug similar to the method depicted in FIG. 18B. Both ends of the implant can be removed from the treatment site by this method.

The embodiments of implants shown in the figures above can be sized and shaped to conform to a treatment site in a patient's tongue, palate or other site in airway-interface tissue and to reside in an orientation and in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. Any embodiment in its elongated state may typically be in the range of about 2 cm to about 10 cm in length in a releasably extended state, and the implant in a contracted state may be in the range of about 1 cm to about 6 cm in length.

Unless defined otherwise, all technical terms used herein have the same meanings as commonly understood by one of ordinary skill in the art to which this invention belongs. Specific methods, devices, and materials are described in this application, but any methods and materials similar or equivalent to those described herein can be used in the practice of the present invention. While embodiments of the inventive device and method have been described in some detail and by way of exemplary illustrations, such illustration is for purposes of clarity of understanding only, and is not intended to be limiting.

Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology.

While some theoretical considerations have been advanced in furtherance of providing an understanding of the invention the claims to the invention are not bound by such theory. Described herein are ways that embodiments of the invention may engage the anatomy and physiology of the airway, generally by opening the airway during sleep; the theoretical consideration being that by such opening of the airway, the implanted device embodiments alleviate the occurrence of apneic events. Moreover; any one or more features of any embodiment of the invention can be combined with any one or more other features of any other embodiment of the invention, without departing from the scope of the invention. Further, it should be understood that while these inventive methods and devices have been described as providing therapeutic benefit to the airway by way of intervention in tissue lining the airway, such devices and embodiments may have therapeutic application in other sites within the body, particularly luminal sites. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method for treating an airway disorder comprising:
providing an implant body having first and second end portions configured to surround first and second spaced apart tissue plugs, respectively;
implanting the body in an airway-interface tissue;
applying tension between the tissue plugs with the implant body to draw the tissue plugs closer together to thereby alleviate tissue obstruction of the airway; and
cutting the first or second end portions to disengage the implant body from the airway-interface tissue.

2. The method of claim 1 where the implanting includes releasably maintaining the implant body in a tensioned configuration for a selected time interval.

3. The method of claim 2 wherein a portion of the implant body is releasably maintained in the tensioned configuration by a bioerodible or biodissolvable material.

4. The method of claim 3 wherein the bioerodible or biodissolvable material is carried about an exterior of the implant body.

5. The method of claim 3 wherein the bioerodible or biodissolvable material is carried within an interior portion of the implant body.

6. The method of claim 1 wherein the applying tension includes releasing the implant body from a tensioned configuration to move toward a non-tensioned configuration.

7. The method of claim 6 wherein the releasing comprises allowing the bioerodible or biodissolvable material to erode or dissolve.

8. A system for revisably treating an airway disorder, comprising:
an implant body configured to conform to an airway-interface tissue site in a manner compatible with normal physiological function of the site, the implant body having a medial portion,
first and second openings extending through first and second implant ends, respectively, for permitting each of the first and second implant ends to surround a tissue plug wherein the first and second implant openings are each formed by a flexible loop at either the first or the second implant end, said flexible loops adapted to surround the tissue plugs and to disengage the implant body from the airway-interface tissue site by releasing the surrounded tissue plugs after the flexible loops have been cut, wherein at least a portion of one of the flexible loops has a higher modulus than that of the medial portion to prevent deformation of the flexible loop under tensioning forces, wherein at least one of the flexible loops comprises a proximal portion of a lower modulus material similar to a modulus of the medial portion of the implant body, and a terminal part having a higher modulus to prevent its deformation under tensioning forces.

9. The method of claim 1, wherein the first and second end portions of the implant body each comprise a loop, and wherein at least a portion of one of the loops has a higher modulus than that of a medial portion of the implant body to prevent deformation of the loop under tensioning forces.

10. The method of claim 1 where the first and second tissue plugs grow through the first and second end portions of the implant body, respectively, after the body is implanted.

11. The method of claim 1 where the first and second end portions are provided in the implant body in a releasably tensioned configuration, the releasably tensioned configuration being releasably maintained by a bioerodible or biodissolvable material carried by a medial portion of the implant body.

12. The method of claim 1 further including cutting said tissue plugs and extracting the implant from the tissue to revise treating.

13. The method of claim 1 further including extracting the implant body from the airway-interface tissue to revise treating.

14. A system for revisably treating an airway disorder, comprising:
an implant body configured to conform to an airway-interface tissue site in a manner compatible with normal physiological function of the site, the implant body having a medial portion,
first and second openings extending through first and second implant ends, respectively, for permitting each of the first and second implant ends to surround a tissue plug wherein the first and second implant openings are each formed by a flexible loop at either the first or the second implant end, said flexible loops adapted to surround the tissue plugs and to disengage the implant body from the airway-interface tissue site by releasing the surrounded tissue plugs after the flexible loops have been cut, wherein at least a portion of one of the flexible loops has a higher modulus than that of the medial portion to prevent deformation of the flexible loop under tensioning forces.

15. The system of claim 14 further comprising a cutting element configured for removal of the implant body from the site.

16. The system of claim 15 wherein the cutting element comprises at least one of a pivotable blade edge, a rotatable sleeve with a blade edge, an axially translatable blade edge, and a cut wire.

17. The system of claim 14 wherein the medial portion is configured for implantation in the airway-interface tissue site in a non-repose condition.

18. The system of claim 17 wherein the medial portion is configured to be releasably maintained in the non-repose condition by a bioerodible or biodissolvable material carried by said medial portion.

19. The system of claim 14 wherein the first and second openings of the first and second implant ends are configured to allow the tissue plugs to grow therethrough after the implant body has been implanted in the airway-interface tissue site.

20. The system of claim 14 wherein the medial portion comprises an elastomeric material.

21. The system of claim 14, wherein the loops comprise an elastomeric material.

22. The method of claim 9, wherein the least one of the loops comprise a proximal portion of a lower modulus material similar to a modulus of the medial portion of the implant body, and a terminal part having a higher modulus to prevent its deformation under tensioning forces.

* * * * *